United States Patent
Thompson et al.

(10) Patent No.: US 6,535,766 B1
(45) Date of Patent: Mar. 18, 2003

(54) IMPLANTED MEDICAL DEVICE TELEMETRY USING INTEGRATED MICROELECTROMECHANICAL FILTERING

(75) Inventors: David L. Thompson, Fridley; Gregory J. Haubrich, Champlin; Steven D. Goedeke, Forest Lake, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 183 days.

(21) Appl. No.: 09/648,604

(22) Filed: Aug. 26, 2000

(51) Int. Cl.⁷ ............................. A61N 1/36; A61N 1/16
(52) U.S. Cl. ............................................ 607/60; 607/32
(58) Field of Search ........................... 607/2, 9, 30, 36, 607/32, 60, 62

(56) References Cited

U.S. PATENT DOCUMENTS

| | | | |
|---|---|---|---|
| 3,311,111 A | 3/1967 | Bowers | 607/30 |
| 3,518,997 A | 7/1970 | Sessions | 607/30 |
| 3,623,486 A | 11/1971 | Berkovits | 607/30 |
| 3,631,860 A | 1/1972 | Lopin | 607/30 |
| 3,738,369 A | 6/1973 | Adams et al. | 607/30 |
| 3,805,796 A | 4/1974 | Terry, Jr. et al. | 607/30 |
| 4,066,086 A | 1/1978 | Alferness et al. | 607/59 |
| 4,208,008 A | 6/1980 | Smith | 714/811 |
| 4,223,679 A | 9/1980 | Schulman et al. | 607/32 |
| 4,233,985 A | 11/1980 | Hartlaub et al. | 352/222 |
| 4,236,524 A | 12/1980 | Powell et al. | 607/30 |
| 4,250,884 A | 2/1981 | Hartlaub et al. | 607/30 |
| 4,253,466 A | 3/1981 | Hartlaub et al. | 607/30 |
| 4,273,132 A | 6/1981 | Hartlaub et al. | 607/28 |
| 4,273,133 A | 6/1981 | Hartlaub et al. | 607/30 |
| 4,374,382 A | 2/1983 | Markowitz | 340/870.01 |
| 4,401,120 A | 8/1983 | Hartlaub et al. | 607/31 |
| 4,520,825 A | 6/1985 | Thompson et al. | 607/59 |
| 4,601,291 A | 7/1986 | Boute et al. | 607/27 |
| 5,052,388 A | 10/1991 | Sivula et al. | 607/22 |
| 5,271,395 A | 12/1993 | Wahlstrand et al. | 607/9 |

*Primary Examiner*—Carl H. Layno
(74) *Attorney, Agent, or Firm*—Girma Wolde-Michael

(57) ABSTRACT

A telemetry receiver for an implantable medical device such as a cardiac pacemaker has an RF antenna coupled to a telemetry circuit that includes an out-of-band rejection filter comprising a microelectromechanical filter. The telemetry circuit further includes an amplifier coupled to the microelectromechanical filter and a demodulator coupled to the amplifier. The filter, amplifier and demodulator are all fabricated on a common integrated circuit die. A multichannel telemetry receiver for an implantable medical device has a plurality of microelectromechanical bandpass filters defining individual channels. A multiplexing circuit selects the signal of an individual bandpass filter channel for application to a demodulator circuit that recovers programming data from a modulated RF transmission from a programming unit. Identification of a preferred data transmission channel for communication of programming data to the implanted medical device is determined by obtaining samples of the signals being passed by each of a plurality of microelectromechanical bandpass filters that define individual channels and evaluating the samples to determine the noise level for each channel. The implantable medical device may be programmed to receive downlink telemetry communications from a programming unit on the channel identified as being the preferred data transmission channel having the lowest noise level.

18 Claims, 8 Drawing Sheets

IMPLANTED MEDICAL DEVICE TELEMETRY USING INTEGRATED MICROELECTROMECHANICAL FILTERING

FIELD OF THE INVENTION

This invention relates to the field of implantable medical devices and particularly to implantable devices that use a high-performance RF telemetry communication link for the transfer of information with an external programming unit.

BACKGROUND OF THE INVENTION

Since the introduction of the first implantable pacemakers in the 1960s, there have been considerable advancements in both the field of electronics and of medicine, such that there is presently a wide assortment of commercially available body-implantable electronic medical devices. The class of implantable medical devices now includes pacemakers, but also implantable cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

As the functional sophistication and complexity of implantable medical device systems have increased over the years, it has become increasingly more important to include a system for facilitating communication between one implanted device and another implanted or external device, for example, a programming console, monitoring system, or the like.

Shortly after the introduction of the earliest fixed-rate, non-inhibited pacemakers, it became apparent that it would be desirable for physicians to non-invasively obtain information regarding the operational status of the implanted device, and/or to exercise at least some control over the device, e.g., to turn the device on or off or adjust the fixed pacing rate, after implant. Initially, communication between an implanted device and the external world was primarily indirect. For example, information about the operational status of an implanted device could be communicated via the electrocardiogram of the patient by modulating the rate of delivery of stimulating pulses in some manner. This was the case for the Medtronic Spectrax™, circa 1979, for which a 10% change in pacing rate was used to indicate battery status. This method could only provide a very low data rate transmission without interfering with the clinical application of the device. An early method for communicating information to an implanted device was through the provision of a magnetic reed switch in the implantable device. After implant, placing a magnet over the implant site would actuate the reed switch. Reed switch closure could then be used, for example, to alternately activate or deactivate the device. Alternatively, the fixed pacing rate of the device could be adjusted up or down by incremental amounts based upon the duration of reed switch closure.

Over time, many different schemes utilizing a reed switch to adjust parameters of implanted medical devices have been developed. See, for example, U.S. Pat. No. 3,311,111 to Bowers, U.S. Pat. No. 3,518,997 to Sessions, U.S. Pat. No. 3,623,486 to Berkovits, U.S. Pat. No. 3,631,860 to Lopin, U.S. Pat. No. 3,738,369 to Adams et al., U.S. Pat. No. 3,805,796 to Terry, Jr., and U.S. Pat. No. 4,066,086 to Alferness et al.

As new, more advanced features have been incorporated into implantable devices, it has been increasingly necessary to convey correspondingly more information to the device relating to the selection and control of those features. For example, if a pacemaker is selectively operable in various pacing modes (e.g., VVI, VDD, DDD, etc.), it is desirable that the physician or clinician be able to non-invasively select a mode of operation. Similarly, if the pacemaker is capable of pacing at various rates, or of delivering stimulating pulses of varying energy levels, it is desirable that the physician or clinician be able to select, on a patient-by-patient basis, appropriate values for such variable operational parameters.

Even greater demands are placed upon the communication system in implantable devices having such advanced features as rate adaptation based upon activity sensing, as disclosed, for example, in U.S. Pat. No. 5,052,388 to Sivula et al. entitled "Method and Apparatus for Implementing Activity Sensing in a Pulse Generator", or in U.S. Pat. No. 5,271,395 to Wahlstrand et al. entitled "Method and Apparatus for Rate-Responsive Cardiac Pacing." The Sivula et al. '388 and Wahlstrand et al. 395 patents are each hereby incorporated by reference herein in their respective entireties.

The information communicated to the implantable device in today's state-of-the-art pacemakers can include: pacing mode, multiple rate response settings, electrode polarity, maximum and minimum pacing rates, output energy (output pulse width and/or output pulse amplitude), sense amplifier sensitivity, refractory periods, calibration information, rate response attack (acceleration) and decay (deceleration), onset detection criteria, and many other parameter settings.

The need to be able to communicate more and more information to implanted devices (i.e., to establish "downlink" communication channels) quickly rendered the simple reed-switch closure arrangement inadequate. Also, it has become apparent that it would also be desirable not only to allow information to be communicated to the implanted device, but also to enable the implanted device to communicate information to the outside world (i.e., to establish "uplink" communication channels). (As used herein, the terms "uplink" and "uplink communication" will be used to denote the communications channel for conveying information from the implanted device to an external unit of some sort. Conversely, the terms "downlink" and "downlink communication" will be used to denote the communications channel for conveying information from an external unit to the implanted device. Although this terminology assumes that communication is occurring between an implanted device and an external device, it is contemplated that the communication system described herein is equally useful and beneficial in situations where communication occurs between any two or more devices, whether some are implanted and others are implanted, or all are implanted, or all are external.)

For diagnostic purposes, it is desirable for the implanted device to be able to communicate information regarding the device's operational status and the patient's condition to the physician or clinician. State of the art implantable devices are available which can even transmit a digitized electrical signal reflecting electrical cardiac activity (e.g., an ECG, EGM, or the like) for display, storage, and/or analysis by an external device. In addition, known pacemaker systems have been provided with what is referred to as Marker Channel™ functionality, in which uplink information regarding the pacemaker's operation and the occurrence of physiological events is communicated to an external programming unit. The Marker Channel™ information can then be printed or displayed in relation to an ECG so as to provide supplemental information regarding pacemaker operation. For example, events such as pacing or sensing of natural heartbeats are recorded with a mark indicating the time of the event relative to the ECG. This is helpful to the physician in interpreting the ECG, and in verifying proper operation of the pacemaker. One example of a Marker Channel™ system is disclosed in U.S. Pat. No. 4,374,382 to Markowitz, entitled "Marker Channel™ Telemetry System for a Medical Device." The Markowitz '382 patent is hereby incorporated by reference herein in its entirety.

Existing systems, which provide a Marker Channel™ output, operate basically by outputting an indication of a physiological or pacemaker event, e.g., a delivered stimulating pulse or a sensed heartbeat, at about the time of the event, thereby inherently providing the timing of the event in relation to the recorded ECG. Alternatively, the Marker Channel™ system can accumulate data over a period of time, e.g., one cardiac cycle, and transmit a batch of data for that interval at the beginning of the next interval. This is what appears to be proposed in U.S. Pat. No. 4,601,291 to Boute et al., entitled "Biomedical System with Improved Marker Channel™ Means and Method."

Typically, communication with an implanted medical device (IMD) has been employed in conjunction with an external programming/processing unit. One programmer for non-invasively programming a cardiac pacemaker is described in its various aspects in the following U.S. Patents to Hartlaub et al., each commonly assigned to the assignee of the present invention and each incorporated by reference herein: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled "Programmable Digital Cardiac Pacemaker with Means to Override Effects of Reed Switch Closure"; U.S. Pat. No. 4,233,985 entitled "Multi-Mode Programmable Digital Cardiac Pacemaker"; U.S. Pat. No. 4,253,466 entitled "Temporary and Permanent Programmable Digital Cardiac Pacemaker"; and U.S. Pat. No. 4,401,120 entitled "Digital Cardiac Pacemaker with Program Acceptance Indicator".

Aspects of the programmer that are the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

Heretofore, three basic techniques have been used for telemetered communication in an implantable device system: magnetic field coupling, reflected impedance coupling, and radio-frequency (RF) coupling. In static magnetic field coupling, of which the above-described Bowers '111 patent is an example, a static magnetic field is generated external to the medical device, e.g., using a permanent magnet, having sufficient strength to close a magnetic reed switch within the implanted device. While such a technique provides a fairly reliable mechanism for turning various functions within the implanted device on or off, the technique is, as noted above, much too slow for efficiently transferring any significant amount of data. Furthermore, for all practical purposes, the static magnetic system is useful only for downlink communication, not for uplink communication. Despite the limitations of magnetic coupling downlink communication, its simplicity and reliability are such that such arrangements can be found even in current devices, for example, the Medtronic Itrel II implantable neural stimulator, as substantially described in U.S. Pat. No. 4,520,825 to Thompson et al.

Dynamic magnetic field programming, on the other hand, relies upon the generation of a series of strong magnetic impulses, which periodically actuate a magnetic reed switch inside the implanted device. The output of the reed switch circuit forms the programming input to data registers in the implantable device, as shown, for example, in the above-referenced to Terry, Jr. et al. '796 patent. Such arrangements have several limitations, including the rate at which strong magnetic impulses can be generated (several hundred hertz or so), the physical size of the reed switch and magnet, the sensitivity to magnetic field orientation, and necessity of generating the impulses in very close proximity to the implanted device.

In a reflected impedance coupling system, information is transferred using the reflected impedance of an internal (implanted) L-R or L-C circuit RF energized by an inductively coupled, external, L-R or L-C circuit. Such a system is shown, for example, in U.S. Pat. No. 4,223,679 to Schulman et al. Advantageously, such a system uses little or no current to transmit information. Disadvantageously, however, the maximum data rate of reflected impedance-coupling systems is relatively slow, and the distance or rate at which information may be transferred is limited.

In RF coupled systems, which are perhaps the most commonly employed communication systems in modern implantable device systems, information is transferred from a transmitting coil to a receiving coil by way of a radio-frequency carrier signal. The carrier signal is modulated with the data that is to be transmitted using an appropriate modulation scheme, such as phase shift keying (PSK), frequency shift keying (FSK), or pulse position modulation (PPM), among numerous others. The modulated carrier induces a voltage in the receiving coil that tracks the modulated carrier signal. This received signal is then demodulated in order to recover the transmitted data. Because the stainless steel or titanium canister commonly used to hermetically enclose an implanted device acts as a low-pass filter for the transmitted RF signals, attenuation increases as frequency is increased. Devices currently on the market have a maximum frequency of less than 200-kHz. Also, the transmitting range has been limited to 2- to 3-inches or so.

High performance telemetry communications systems used in sensor and signaling applications allow a high level of integration, as every component of the telemetry system is realized in a single semiconductor integrated circuit. The lack of external tuned circuits in such telemetry systems dictates the use of a very broadband receiver front end with a high dynamic range, which makes the receiver especially susceptible to strong out-of-band electromagnetic interference (EMI) from such sources as television, FM and business bands, and two-way, cellular, or PCS radio transmitters. Though intermittent, EMI may potentially degrade the telemetry communications link. Additionally, EMI may overload or interfere with the implant's sensors and sensor amplifiers thereby causing spurious therapy outputs, or inhibiting required therapy output, based on erroneous sensor data. High-level (order) EMI interference detectors may be used to inhibit spurious therapy in this case. Alternately, RF (low-pass, high-pass, or notch) filtering can also be applied to sensor inputs of the implant to filter out the EMI interference and retain normal device performance. However, retaining full telemetry link performance under large EMI interference requires attenuation of the interfering signal while not attenuating the telemetry signal. Typically this is done via RF band-pass filtering at the receiver front-end for strong out-of-band interferors. Additionally, a very narrow (at least one channel bandwidth) tunable preselector (band-pass) filter, or an RF notch filter can be used to reject narrow in-band or out-of-band interference. In this way, EMI interference to the telemetry link can be minimized or eliminated The majority of front end high Q bandpass filters used in radio frequency (RF) and intermediate frequency (IF) stages of heterodyning transceivers use off-chip, mechanically resonant components such as crystal filters, helical filters, or surface acoustic wave (SAW) resonators. These greatly outperform comparable devices using transistor technologies in terms of insertion loss, percent bandwidth, and achievable rejection of noise signals. SAW resonators can be combined with signal processing and spread spectrum technologies for high rejection against jamming and interference. Advantages are high sensitivity, high reliability, and a moderate size of 1 cm$^2$.

Off-chip components are required to interface with integrated components at the board level, which constitutes an important bottleneck to miniaturization and the performance of heterodyning transceivers. Recent attempts to achieve single chip transceivers have used direct conversion architectures, rather than heterodyning and have suffered in overall performance. The continued growth of micromachining technologies, which yield high-Q on-chip vibrating mechanical resonators now make miniaturized, single-chip heterodyning transceivers possible. Microelectromechanical (MEMS) resonators yield ultra high Qs of over 80,000 under vacuum and center frequency temperature coefficients less than 10 ppm/° C. and serve well as a substitute for crystal filters and SAW devices in a variety of high-Q oscillator and filtering applications. MEMS resonators are capable of frequency operation to GHz levels and filtering operation up to the 6$^{th}$ order.

SUMMARY OF THE INVENTION

The present invention provides an implantable medical device, such as a cardiac pacemaker, having an RF transceiver that uses a microelectromechanical filter as an out-of-band interference rejection filter. The microelectromechanical filter is preferably implemented as a receiver front-end bandpass filter or notch filter. Yet further, the present invention provides an implanted medical device having a multichannel RF transceiver wherein each channel includes a microelectromechanical filter and wherein a processor evaluates the noise level on each channel and selects the channel having the best signal-to-noise ratio for further communications.

The present invention yet further contemplates the use of microelectromechanical filters in the RF transceiver of an external programming unit that communicates with an implanted medical device. Moreover, a microelectromechanical filter may be used in each channel of a multichannel RF transceiver in an external programming unit.

BRIEF DESCRIPTION OF THE DRAWINGS

FIG. 5b is an equivalent model of the microelectromechanical filter of FIG. 5a.

DETAILED DESCRIPTION OF PREFERRED EMBODIMENTS

Figure 1:
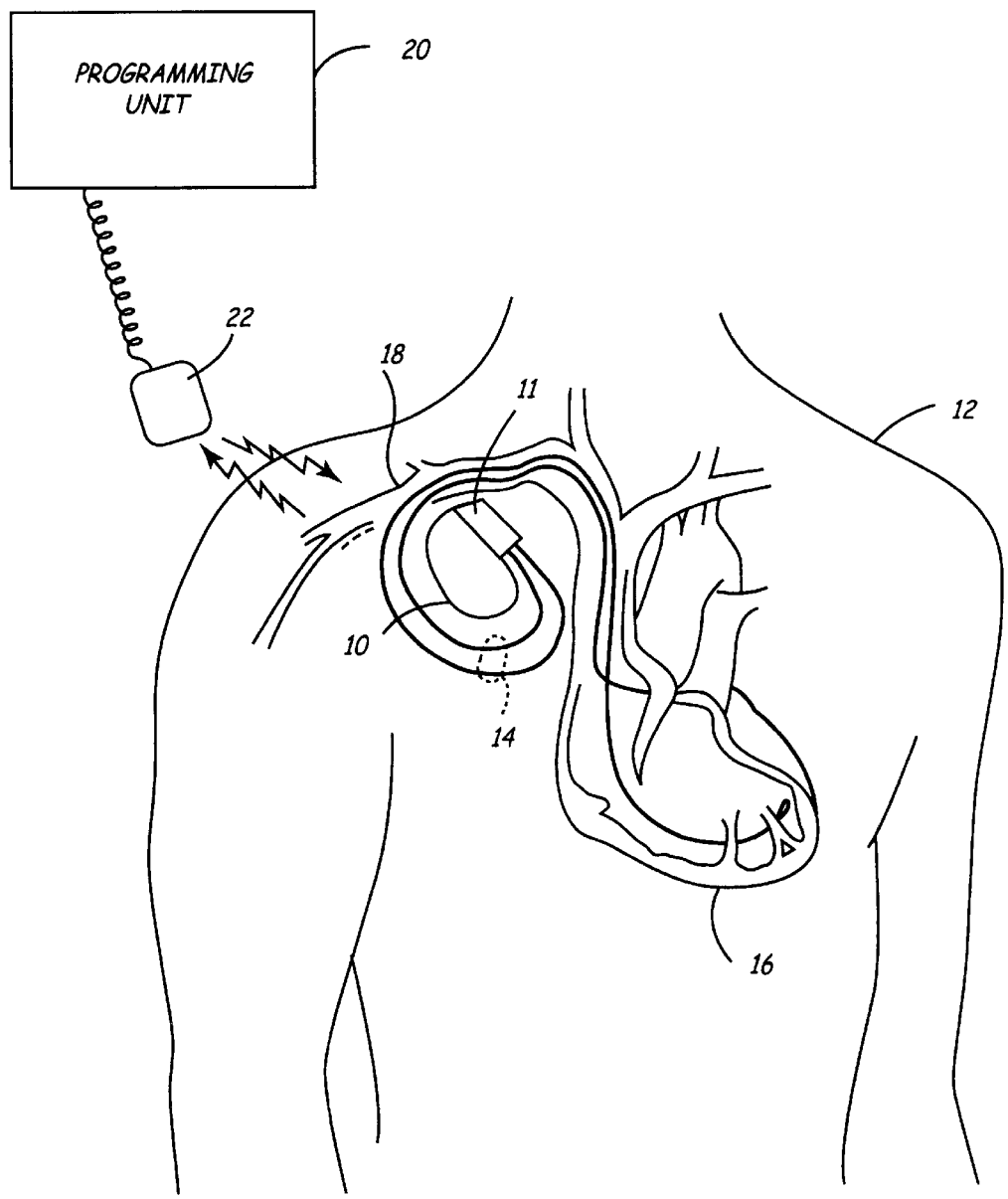
FIG. 1 is an illustration of an implanted medical device in the form of a cardiac pacemaker and an associated external programming unit.

The implantable medical device (IMD) system shown in FIG. 1 includes, for example, an implantable pacemaker 10, which has been implanted in a patient 12. The pacemaker 10 is housed within a hermetically sealed, biologically inert outer canister or housing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals or delivering electrical pacing stimuli to the heart 16. The leads 14 may be implanted with their distal end situated in either the atrium or ventricle of the heart 16.

Although the present invention is described herein in an embodiment that includes a pacemaker, it may be advantageously embodied in numerous other types of implantable medical device systems in which it is desirable to provide a communication link between two physically separated components.

FIG. 1 also depicts an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between pacemaker 10 and programmer 20. In many known implantable device systems, a programming head such as that depicted in FIG. 1 is positioned on the patient's body over the implant site of the device (usually within 2- to 3-inches of skin contact), such that one or more antennas within the head can send RF signals to, and receive RF signals from, an antenna disposed within the hermetic enclosure of the implanted device or disposed within the connector block of the device, in accordance with common practice in the art.

Figure 2:
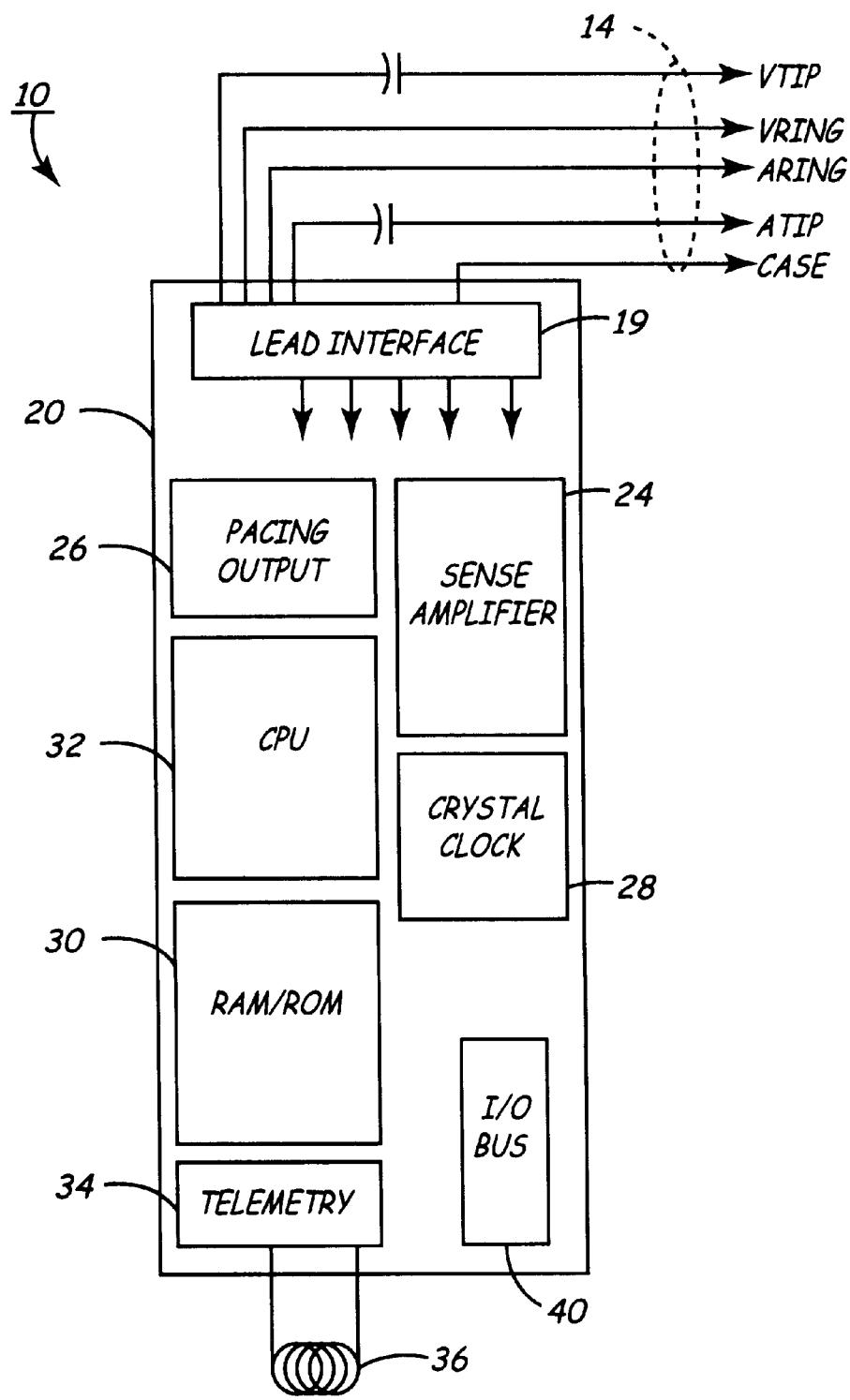
FIG. 2 is a block diagram depicting the various functional circuit blocks of the implanted pacemaker of FIG. 1.

FIG. 2 provides a block diagram of the electronic circuitry that makes up pacemaker 10 for delivery of electrical stimulation therapy to the patient in accordance with the presently disclosed embodiment of the invention. FIG. 2 shows that pacemaker 10 comprises circuitry for controlling the device's pacing and sensing functions. The pacemaker circuitry may be of conventional design, in accordance, for example, with what is disclosed the above-referenced Sivula et al. '388 patent. To the extent that certain components of the circuitry of pacemaker 10 are conventional in their design and operation, such components will not be described herein in detail, as it is believed that design and implementation of such components would be a matter of routine practice to those of ordinary skill in the art. For example, the circuitry of pacemaker 10 shown in FIG. 2 includes sense amplifier circuitry 24, stimulating pulse output circuitry 26, a crystal clock 28, a random-access memory and read-only memory (RAM/ROM) unit 30, and a pacing timing and control circuit in the form of a programmed central processing unit (CPU) 32, all of which are well-known in the art.

Pacemaker 10 also includes internal telemetry communication circuit 34 coupled to antenna 36 so that it is capable of communicating with external programmer/control unit 20, as will be hereinafter described in greater detail. Various telemetry systems for providing the necessary uplink and downlink communication channels between an external programming unit and an implanted pacemaker have been shown in the art. Communication telemetry systems are disclosed, for example, in the following U.S. Patents: U.S. Pat. No. 4,539,992 to Calfee et al. entitled "Method and Apparatus for Communicating With Implanted Body Function Stimulator;" U.S. Pat. No. 4,550,732 to Batty Jr. et al. entitled "System and Process for Enabling a Predefined Function Within An Implanted Device;" U.S. Pat. No. 4,571,589 to Slocum et al. entitled "Biomedical Implant With High Speed, Low Power Two-Way Telemetry;" U.S. Pat. No. 4,676,248 to Berntson entitled "Circuit for Controlling a Receiver in an Implanted Device;" U.S. Pat. No. 5,127,404 to Wyborny et al. entitled "Telemetry Format for Implanted Medical Device;" U.S. Pat. No. 4,211,235 to Keller, Jr. et al. entitled "Programmer for Implanted Device;" the above-referenced Markowitz '382 patent; and U.S. Pat. No. 4,556,063 to Thompson et al. entitled "Telemetry System for a Medical Device." The Wyborn et al. '404 patent and the Thompson et al. '063 patent are hereby incorporated by reference herein in their respective entireties.

With continued reference to FIG. 2, pacemaker 10 is coupled to one or more leads 14 which, when implanted, extend transvenously between the implant site of pacemaker 10 and the patient's heart 16, as previously noted with reference to FIG. 1. Physically, the connections between leads 14 and the various internal components of pacemaker 10 are facilitated by a conventional connector block assembly 11, shown in FIG. 1 but not shown in FIG. 2. Electrically, the coupling of the conductors of leads and internal electrical components of pacemaker 10 may be facilitated by a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pacemaker 10 are not shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, the circuitry of pacemaker 10 includes central processing unit (CPU) 32 which may be an off-the-shelf programmable microprocessor or microcontroller, but in the presently preferred embodiment of the invention is a custom integrated circuit. Although specific connections between CPU 32 and other components of the pacemaker circuitry are not shown in FIG. 2, it will be apparent to those of ordinary skill in the art that CPU 32 functions to control the timed operation of stimulating pulse output circuit 26 and sense amplifier circuit 24 under control of program of instructions stored in RAM/ROM unit 30. Crystal oscillator circuit 28 in the presently preferred embodiment is a 32,768-Hz crystal controlled oscillator that provides main timing clock. Again, the lines over which such clocking signals are provided to the various timed components of pacemaker 10 (e.g., microprocessor 32) are omitted from FIG. 2 for the sake of clarity. It is believed that those of ordinary skill in the art will be familiar with such an operative arrangement.

It is to be understood that the various components of pulse generator 10 depicted in FIG. 2 are powered by means of a battery (not shown), which is contained within the hermetic enclosure of pacemaker 10, in accordance with common practice in the art. For the sake of clarity in the drawings, the battery and the connections between it and the other components of pacemaker 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

Sense amplifier circuit 24, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety; functions to receive electrical cardiac signals from leads 14 and to process such signals to derive event signals reflecting the occurrence of specific cardiac electrical events, including atrial contractions (P-waves) and ventricular contractions (R-waves). These event-indicating signals are provided to CPU 32 for use by the CPU in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of telemetry block 34 in pacemaker 10, and an associated RF transceiver in external programming unit 20.

Figure 3:
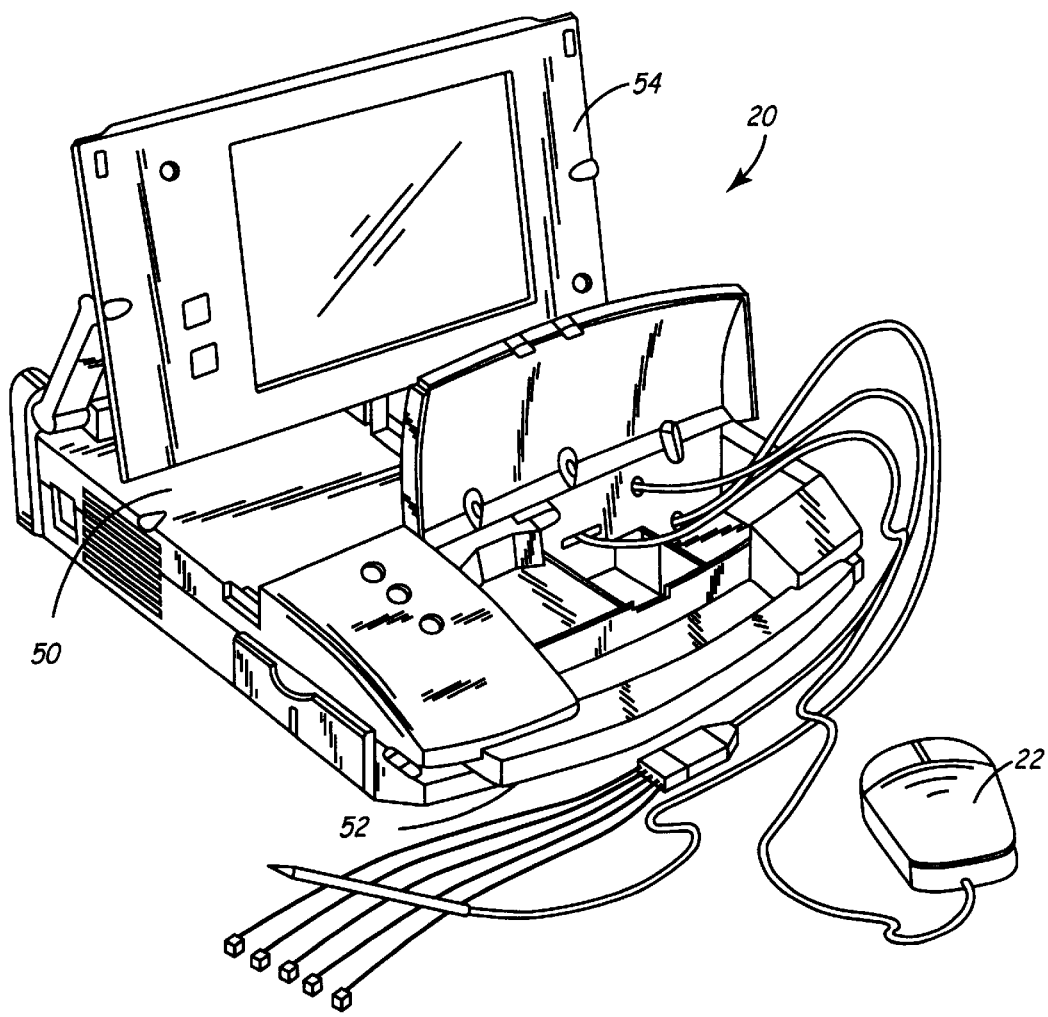
FIG. 3 is a perspective view of the external programming unit of FIG. 1.

FIG. 3 shows a perspective view of a programming unit 20 in accordance with the presently disclosed embodiment of the invention. Internally, programmer 20 includes a processing unit (not shown in the Figures), which in accordance with the presently disclosed embodiment of the invention is a personal computer type motherboard, e.g., a computer motherboard including an Intel 80×86 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 3, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 54 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for programmer 20 to adapt its mode of operation depending upon the type of implanted device to be programmed. Accordingly, it may be desirable to have an expansion cartridge containing EPROMs or the like for storing program information to control programmer 20 to operate in a particular manner corresponding to a given type of implantable device.

In accordance with the presently preferred embodiment of the invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

Display screen 64 is operatively coupled to the computer circuitry disposed within housing 60 and is adapted to provide a visual display of graphics and/or data under control of the internal computer.

Programmer 20 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 4:
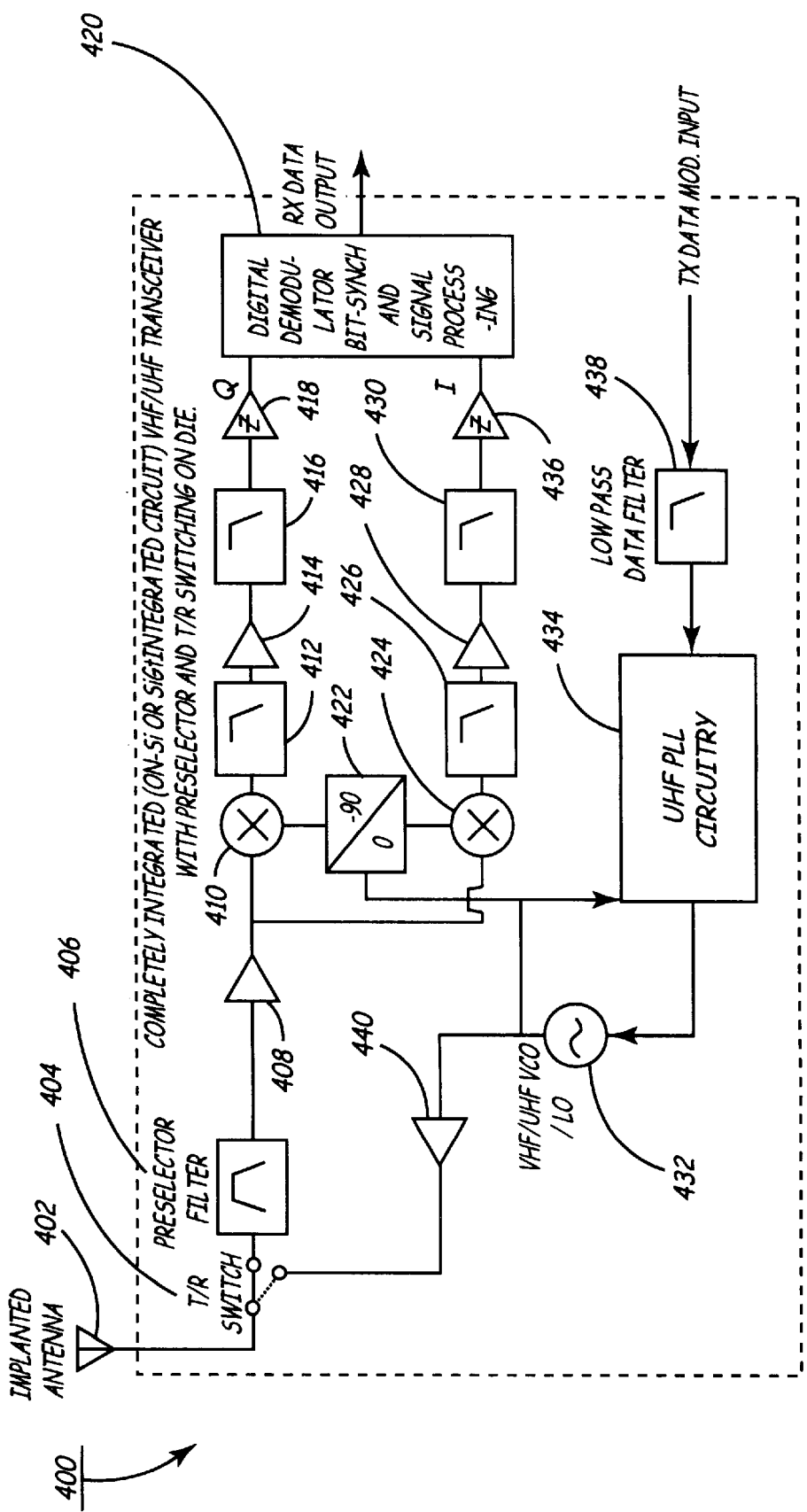
FIG. 4 is a block diagram of an RF telemetry transceiver for the telemetry circuit functional block shown in FIG. 2.

An RF transceiver for use as the telemetry block 34 in pacemaker 10 is shown in FIG. 4. The UHF RF Transceiver shown in FIG. 4 consists of the following main functional blocks: a "Zero-IF" Receiver (404 through 430 and 436), an FSK Transmitter (438 and 440), and a UHF Frequency Synthesizer 432 & 434) providing both Local Oscillator injection to the receiver's UHF mixer and a FM modulated frequency source for the transmitter.

The Zero-IF Receiver consists of a T/R switch (404) (RF switching transistor structure, or an RF MEMS switch) to route the RF energy received from the Implanted Antenna (402) to the Preselector Filter (406). The Preselector Filter may consist of either a UHF SAW Bandpass Filter or an RF MEMS Bandpass Filter. The SAW Filter would be external to the die, while the RF MEMS Filter could be integrated on the RF IC die. The function of the Preselector Filter is to reject all out-of-band RF signals such as AM, FM, TV Broadcasting, Two-way Radio, and Cellular Phones, etc., and allow only the desired Telemetry Frequency Band of interest to pass unattenuated to the receiver's Low Noise Amplifier, or LNA, (408) input. This prevents strong RF interference from overloading the receiver's RF front-end, while allowing the weaker telemetry signal to be received with no apparent interference.

The LNA has a very low inherent noise floor and amplifies the desired weak RF telemetry signal prior to sending it on to the two UHF Mixers (410 and 424). As seen in FIG. 4, the LNA output is fed equally to two UHF Mixers. The purpose of two mixers is to generate INPHASE and QUADRATURE baseband IF (Intermediate Frequency) signals which can be processed for an FM demodulation function. The INPHASE Mixer (410) has the LO injection phase shifted -90 degrees by the LO phase-shifter (422), with the QUADRATURE Mixer (424) having the LO fed INPHASE from the LO phase-shifter. The baseband output of these two mixers are thus in phase quadrature with each other (an I and a Q IF channel). The IF filtering and amplification occur in two identical parallel paths: one containing the I Channel, and the second the Q Channel. The UHF Mixer outputs feed two "roofing filters" (412 & 426), which consist of an on-chip active low-pass filter slightly wider than the channel bandwidth (these filters could also be implemented as a low frequency MEMS bandpass filters). These filters improve the apparent Intermodulated Distortion performance of the following IF stages. The signal flows from the roofing filter output to two IF amplifiers (414 & 428) which amplify the IF signal prior to filtering by the IF channel low-pass filters (416 & 430) which set the effective communications channel bandwidth. These filters are currently on-chip active low-pass filters, but they could also be implemented with on-chip lower frequency bandpass filters.

The output of the IF channel filters is passed to the limiter amplifiers (418 & 436) which amplify the downconverted and filtered received signal until limiting occurs. This digital signal is then processed via the digital signal processing in the Digital Demodulator, Bit-Sync, and Signal Processing circuitry (420) to provide both serial data output and a synchronous clock output.

The UHF Frequency Synthesizer (432 & 434) is a single loop phase locked loop which phase locks the UHF VCO (432) to a crystal reference oscillator. The frequency control element for the open-loop UHF VCO may be an on-chip, or off-chip, L-C tank with varactor tuning, or an on-chip tunable RF MEMS resonator. The PLL uses programmable dividers to provide for channel changes and control of the UHF VCO via a closed loop control system using the UHF VCO frequency control input as the control means.

The UHF Transmitter simply takes the output of the frequency synthesizer, amplifies it (via 440), and sends it through the T/R switch to the Implanted Antenna. TX modulation is accomplished my directly Frequency Modulating the UHF VCO via a Lowpass Data Filter (438) to limit the transmitter bandwidth.

Figure 5A:
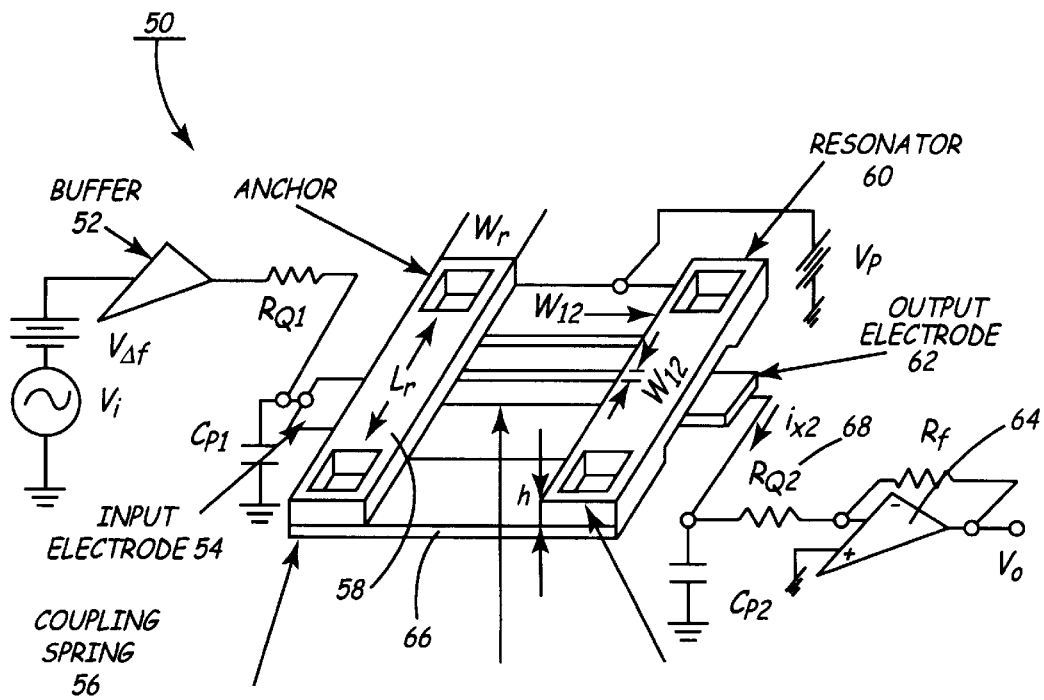
FIG. 5a is a perspective view of a layout for a microelectromechanical filter for use as an out-of-band interference rejection filter.

FIG. 5a provides a perspective view of a high-frequency microelectromechanical (MEM) filter proposed for use as the bandpass filter in the RF telemetry transceiver 400 of an implanted medical system 10. The fabrication of which is described in U.S. Pat. No. 5,455,547; 5,491,604; 5,589,082; and 5,839,062; all of which are incorporated herein in their entirety. The filter 50 consists of two microelectromechanical beamed resonators 58 and 60, coupled mechanically by a soft spring 56 and suspended 0.1 $\mu$m above the piezoelectric substrate 66. Conductive polysilicon strips underlie the central regions of each resonator and serve as capacitive transducer electrodes (input electrode 54 and output electrode 62) positioned to induce resonator vibrations perpendicular to the substrate. The resonator-electrode gaps are determined by the thickness of an oxide spacer during fabrication and can thus be made small (0.2 $\mu$m or less) to maximize electromechanical coupling.

In normal operation, the filter 50 receives a signal applied to the input electrode 54. The filter output signal is taken at the other end of the structure at the output electrode 62. Upon application of a signal to input electrode 54, which has a suitable frequency content, from buffer amplifier 52, the resonators 58 and 60 begin to vibrate in one or more flexural modes, perpendicular to the substrate 66. If the signal has a frequency within the bandpass, both resonators vibrate. Vibration of the output resonator 60 is coupled to the output electrode 62 to provide an output current $i_{x2}$. The current $i_{x2}$, is then directed to the resistor 68, which provides the proper termination impedance for the microelectromechanical filter. Resistor $68_{then}$ feeds a transresistance amplifier 64 to amplify $i_{x2}$ to a buffered output voltage $V_0$.

Figure 5B:
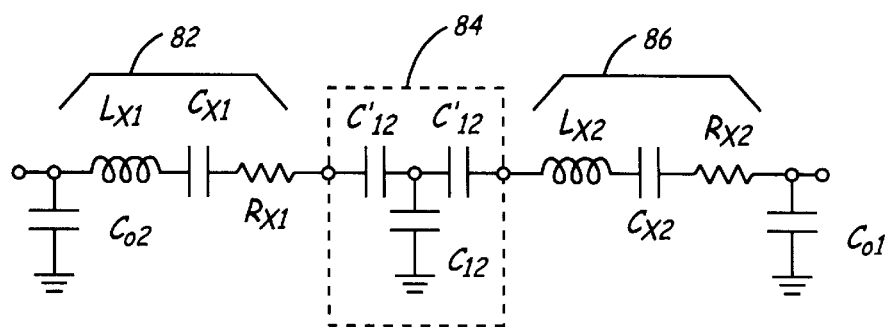

If each resonator has the same resonance frequency, the center frequency of the overall filter has that frequency. The coupling spring 56 acts to pull the resonator frequencies apart, creating two closely spaced resonance modes that constitute the filter passband. Thus the center frequency of a mechanical bandpass filter is determined mainly by the geometry of the constituent resonators, while its bandwidth is determined by the coupling spring 56. To properly design the resonators 58 and 60 and coupling spring 56 topology, the electrical domain inductance and capacitance or a properly synthesized LC ladder filter are utilized via analogous values of compliance and mass in the mechanical domain. As shown in FIG. 5b, the resonators (58 and 60) in the mechanical domain equate to LCR tanks (82 and 86) in an equivalent electrical circuit, while the coupling spring 56 is analogous to coupling capacitors 84.

Figure 6:
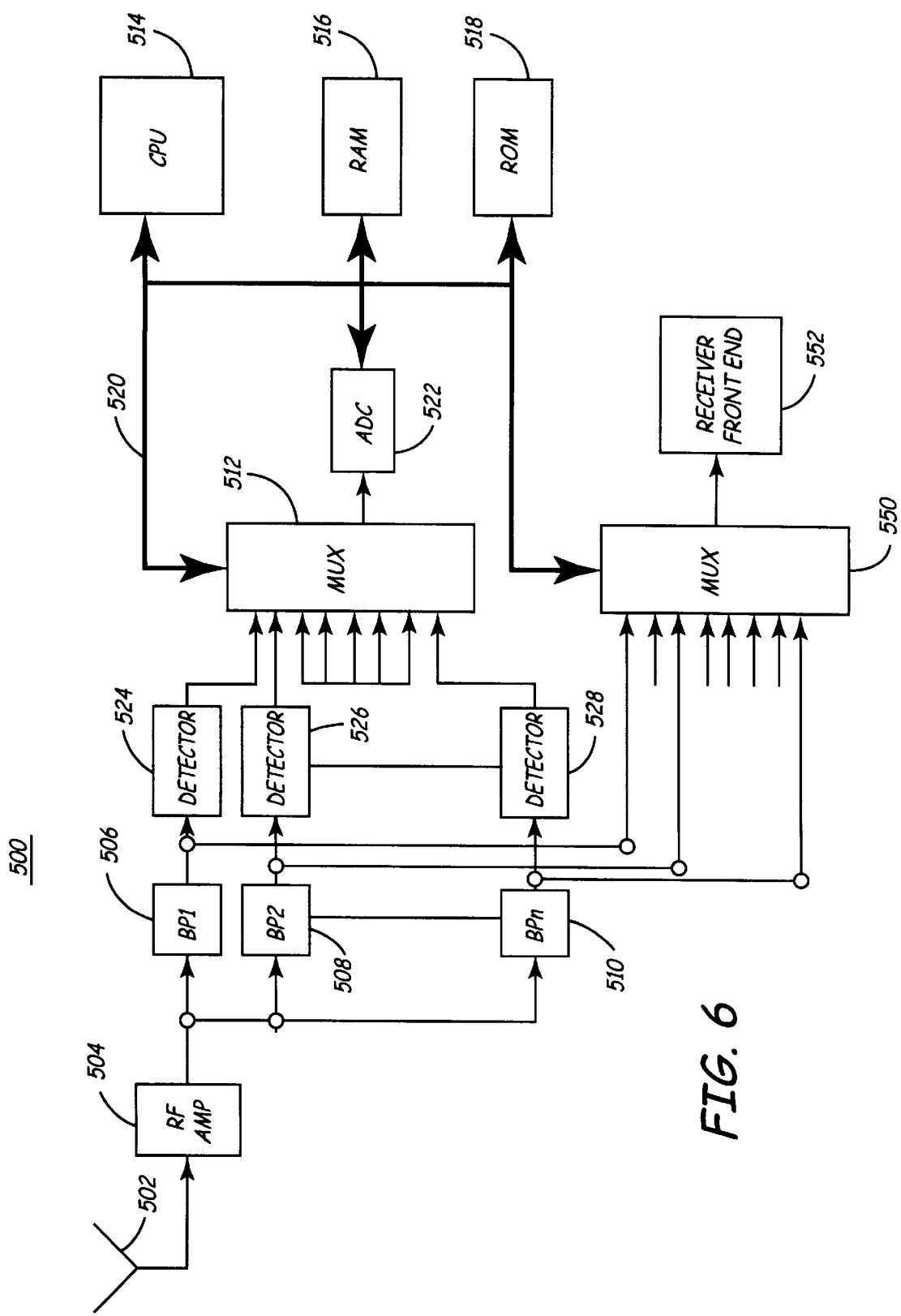
FIG. 6 is a block diagram of a multichannel RF telemetry receiver for use in the implantable pacemaker and/or the external programming unit of FIG. 1 and depicting the use of a microelectromechanical filter in the front end of each channel.

FIG. 6 is a schematic block diagram of an arrangement of multiple receivers that together form a multichannel RF telemetry receiver 500, used to receive and process incoming RF signals. The broadband RF amplifier 504 is configured to receive RF signals from the antenna 502. The microelectromechanical (MEM) bandpass filter 506 and RF detector 524 are used for default frequency telemetry operations. The remaining microelectromechanical bandpass filters and RF detectors 508/526 and 510/528 are tuned to individual channels in a band of 402–405 MHz (e.g., 403 MHz and 405 MHz). Although only two filter/detector circuits are shown, the number of such "receiver" or "channels" can be expanded. The RF detector outputs are coupled as inputs to a multiplexing circuit (MUX) 512. The selected MUX input is established under control of the microprocessor 514 and the program stored in ROM 518 and/or RAM 516. The MUX output is coupled to an analog-to-digital converter (ADC) 522 that provides a digitized value of the signal being passed by the selected filter. The processor 514 operating in accordance with a set of program instructions evaluates the noise level of the receiver channel. Each receiver channel is evaluated before a determination is made as to which channel has the lowest noise level. Thereafter, the output of the bandpass filter in the channel having the best lowest noise and presenting the best signal-to-noise ratio (SNR) is routed through a second multiplexing circuit 550 to the front end 552 of the data receiver. Further communications take place on the selected channel. If desired, the processor can continue to monitor the noise level of the selected channel for suitable quality of the link. If the noise level does not remain below a monitoring noise threshold according to a predetermined criterion, communications can be shifted to a different receiver channel to determine whether a lower noise level condition can be found for further communications.

The sampling of filtered signals on each channel and an evaluation of the channel noise level can be made using just the ambient signals obtained through antenna 502 and broadband amplifier 504 without a specific RF transmission from the other device. For example, in the programming unit, a test routine can be run wherein the channels are scanned for interference measurement purposes in the absence of an uplink transmission from the implanted medical device. The channels are then ranked according to the general level of noise appearing in the passband of each channel. Or, the channel quality evaluation can be made on the basis of an uplink transmission on each frequency channel and an actual measurement made of the SNR of each channel. The later approach, of course, requires that a tunable transmitter be provided in the implanted medical device. Also, a spectrum analyzer is normally employed to measure the power of the combined signal and noise.

Figure 7:
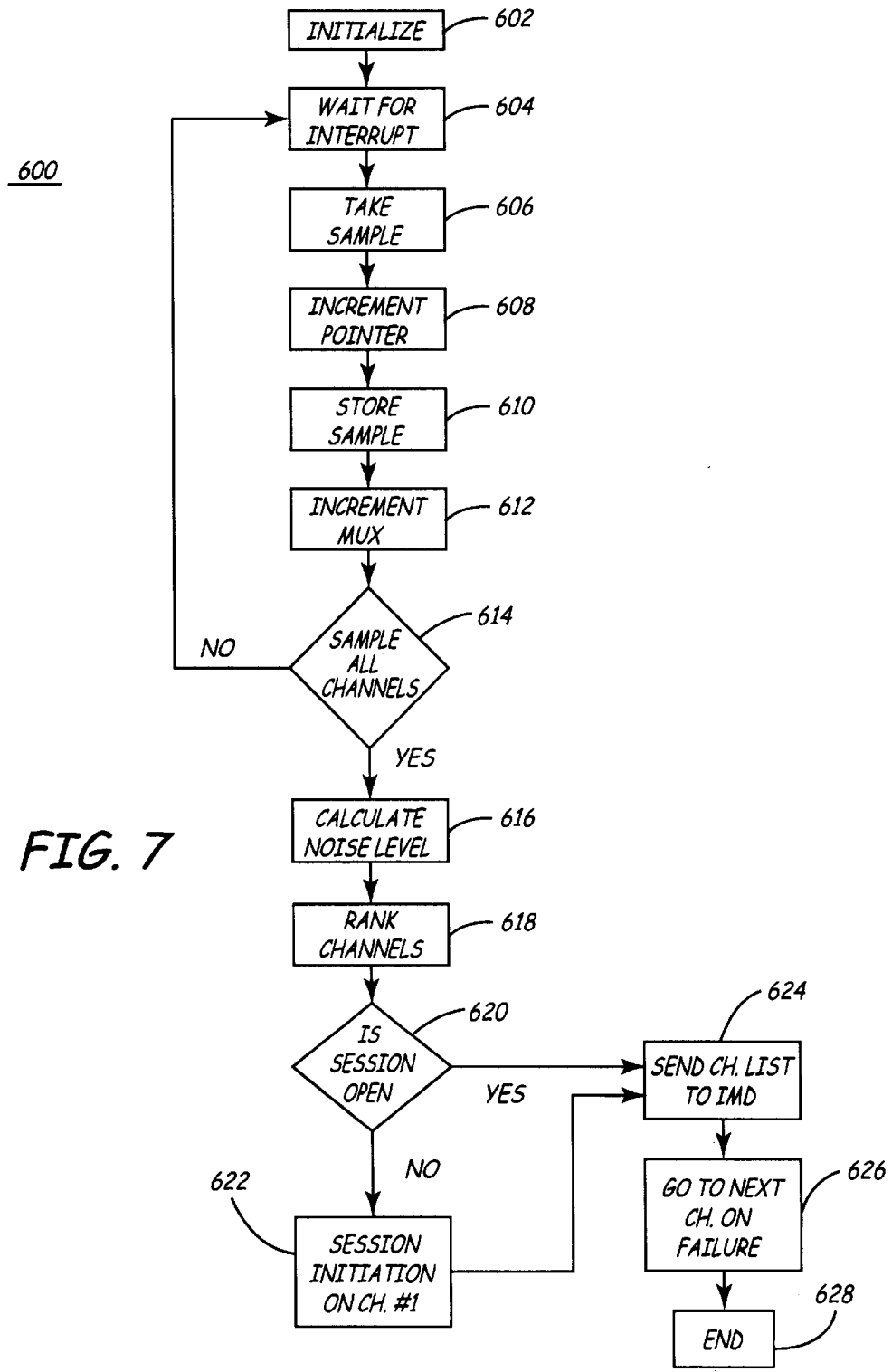
FIG. 7 is a flow diagram outlining the steps in a microprocessor executable routine for evaluating the signal-to-noise ratio of each channel of the receiver shown in FIG. 6 and for selecting the receiver channel having the best performance.

FIG. 7 is a flow diagram 600 depicting a set of instructions in a routine to be executed by the microprocessor in making the evaluation and channel selection. In general, after initialization, when an interrupt occurs, the microprocessor samples the signals present in each of the bandpass filtered channels. The sample is stored in an accumulator within the microprocessor. The microprocessor calculates the noise levels for each channel and then ranks the channels before selecting the channel with the lowest noise level for communication.

In the case of a programming unit, initialization at block 602 may occur upon power being applied to the programmer 20 or upon the start of a new communication link to an IMD 10. A telemetry communication link is established by placing the programming head over the implant site. The processor then waits for a system interrupt at block 604 generated from a timer, a user entered keystroke or pen input, or a flag being set from other software programs. The ADC takes a sample of the link noise levels 606, increments a pointer 608, stores the converted value in the accumulator 610. The MUX is stepped to the next channel 612. Also, if the IMD is being stepped to a corresponding transmission frequency, an indication is sent to shift transmission to the next frequency.

At block 614, if all channels have not been sampled, the routine returns to block 604. However, if at block 614 all channels have been sampled, the routine advances to the functional step 616 of calculating the noise levels of all channels. Based upon the calculations of noise, the channels are ranked in order of SNR or general level of noise in the passband. If a communication session with the IMD has been opened previously as indicated by a flag set at block 620, the routine at block 624 directs the programmer to send the rank order list of channel preference to the IMD. The programming unit and IMD then continue link operation on the highest ranked channel. If the link is lost and/or the SNR decreases below some preset value, both switch to the next ranked channel in accordance with block 626. If after, for example, 2 channels have been lost, the programmer will automatically re-initialize the link search routine at block 602. If at block 620 the session has not been open, the session is initialized using channel #1 as the default channel and the list of channels according to rank is sent to the IMD at block 622.

In the case of a multichannel receiver in an IMD, initialization may occur upon detection of an RF signal transmission from the programmer on the default channel. This detection signals the IMD that a communication session is being established and a determination of suitable receiver channel quality is to be undertaken. Thereafter, the IMD sends an acknowledgement command to the programmer and switches to the next receiver channel to obtain a noise level sample of signals appearing within that frequency band. After the IMD captures a sample of the signal on that channel for analysis, it signals the programmer an acknowledgement that it is switching to the next channel. The procedure continues until signals for all receiver channels have been sampled. Following the last acknowledgement, the IMD and programmer go to the default channel. The IMD evaluates the noise levels of the channels and selects a particular channel for the communication session with the programmer. The IMD sends the programmer an indication of the selected channel and switches to that channel to receive further communications from the programming unit in the communications session. The programmer, upon reception of the indication of the selected channel, makes further transmissions of information during the communication session with the IMD on that channel.

The frequency switching protocol followed by the IMD and programming unit may also be implemented using a sequence of internally timed steps that serve to automatically switch both the IMD receiver and the programming unit transmitter from channel to channel without intervening acknowledgements being sent from the IMD to the programmer.

Another approach to evaluating the noise level on multiple communications channels could be to have the programmer control the channel switching of the IMD receiver by sending commands to switch channels. Thus, after the initial transmission on the default channel and acknowledgement by the IMD, the programmer may send a command to the IMD to switch to the next channel. After a delay sufficient for the IMD to acquire a data sample for noise level analysis, the programmer again commands the IMD to switch to the next channel. The procedure continues until signal samples on all receiver channels have been obtained. The programmer may then interrogate the IMD to determine which channel has been selected for further communication transmissions.

Another protocol that could be followed is to have the IMD obtain channel signal samples and uplink them to the programmer for evaluation and channel selection determination. In this protocol, the programming unit receiver may also undertake to simultaneously sample noise level on each channel and evaluate them along with the noise level samples obtained by the IMD. In this protocol, therefore, the noise level on each receiver channel can be evaluated from the standpoint of both the IMD and the programming unit receivers. The programmer can then make an evaluation and select a channel for further communication transmissions that takes into consideration the best channel from the standpoint of both the reception of the downlink transmission to the IMD and the reception of the uplink transmission to the programmer.

Figure 8:
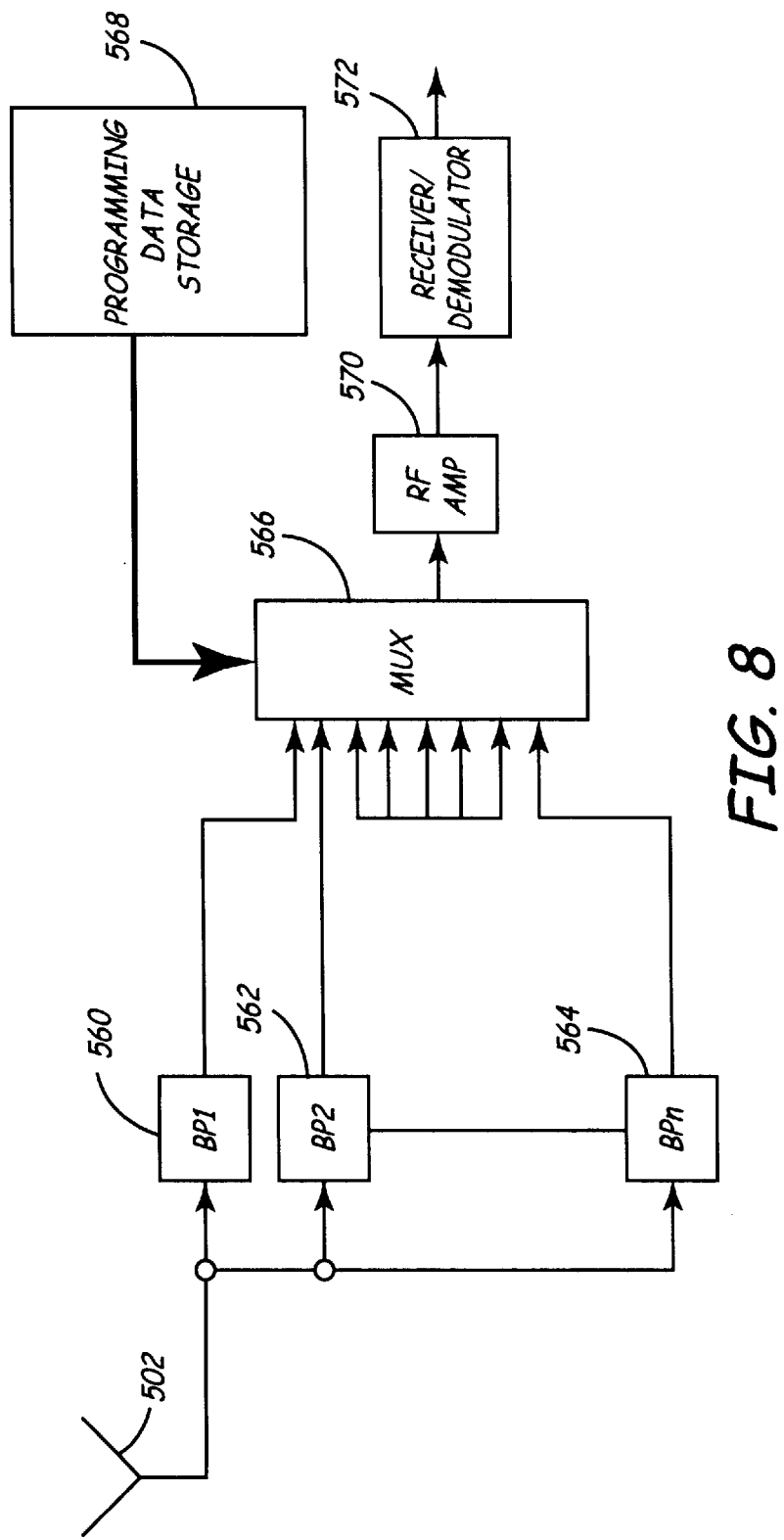
FIG. 8 shows another embodiment of a multichannel receiver for an implantable pacemaker, which does not include the channel noise level evaluation function.

In FIG. 8, another embodiment of a multichannel receiver for an IMD is shown which does not include the channel noise level evaluation function. In this embodiment, an array of microelectromechanical bandpass filters 560–564 is coupled to the RF antenna in the fashion of FIG. 4. The filter outputs are applied as inputs to a multiplexing circuit 566. Based upon an input from the programming data storage 568, which could be part of ROM/RAM 30 shown in FIG. 2, multiplexing circuit 566 selects the output of one of the bandpass filters. Signals from the selected bandpass filter are routed through to the RF amplifier 570 and the receiver/demodulator circuit 572. Both amplifier 570 and receiver/demodulator 572 may be circuitry in accordance with the receiver shown in FIG. 4.

Using the multichannel receiver embodiment of FIG. 8 in conjunction with a programming unit providing multichannel noise level evaluation in accordance with the circuitry of FIG. 6 and the operational sequence outlined in FIG. 7 permits the IMD to receive channel selection data as another item of programming data. All channel noise level evaluation and determination is preferably done in the programming unit. It is, however, to be recognized that the individual functions of channel data sampling, channel noise level evaluation, and channel selection can be split between the programming unit and the IMD. For example, the channel data samples obtained by the programming unit might be sent along with programming data to the IMD for IMD to do the noise level evaluation and make channel selection determination.

The term signal-to-noise ratio is being used in its common ordinary meaning to those skilled in the art of telecommunications. Because transmitted signals are actually voltages or currents having some varying property that carries intelligence, any other voltages or currents that interact with the signals will tend to mask the intelligence. The unwanted voltages or currents are grouped together under the characterizations of noise and interference. In practical application, some noise is always present and cannot be eliminated completely. As long as the signal strength is sufficiently greater than the noise strength, the signal intelligence will be recoverable. The ratio of the signal strength to the noise strength is obtained by dividing a measurement of the signal strength by a measured value of the noise strength. This is expressed as (S+N)/N. To get true the signal-to-noise ratio, it is necessary to subtract N from (S+N) to obtain S/N. This can be expressed in terms of voltage or power and may be peak values or effective values. High signal-to-noise ratios are desirable because they mean that the noise strength is much weaker than the signal strength and the accuracy of the recovered intelligence is higher. Low signal-to-noise ratios indicate that the noise strength is close to the signal strength and accuracy of the recovered intelligence is compromised. Considerations of making measurements of RF power using a superheterodyne spectrum analyzer are discussed in Hill et. al., "Accurate Measurement of Low Signal-to-Noise Ratios Using a Superheterodyne Spectrum Analyzer," IEEE Transactions on Instrumentation and Measurement, Vol. 39, No. 2, April, 1990.

Federal Communications Commission Regulations found in 47 C.F.R. include provisions that obtain with respect to medical device implant communications in the 402–405

MHz frequency band. These provisions include what is referred to as the "Medical Implant Communications Service" (MICS) and address certain performance characteristics of a communications channel to be used for RF communications with an implanted medical device. The performance characteristics criteria set forth in Section 95.628 can be adopted for determination of the selected channel. Generally, the requirement for an acceptable data transmission channel is that, based on use of an isotropic monitoring system antenna, the monitoring threshold power level must not be more than 10 log B (Hz)–150 (dBm/Hz)+ G(dBi), where B is the emission bandwidth and G is the medical implant programmer transmitter antenna gain relative to an isotropic antenna. The emission bandwidth B is measured as the width of the signal frequency content between points on either side of the carrier center frequency that are 20 dB down relative to the maximum level of the modulated carrier.

While the present invention has been described herein with reference to particular, preferred embodiments and applications thereof, numerous variations and modifications could be made thereto by those skilled in the art without departing from the spirit and scope of the invention as claimed. Accordingly, the scope of the invention should be determined with reference to the claims set forth below.

What is claimed is:

1. An implantable medical device operating in accordance with programming data received over a downlink communications channel established by a modulated RF transmission sent from an external programming unit, comprising:
    an electrical stimulation therapy delivery circuit disposed within a hermetically sealed housing adapted for implantation in the body of a patient;
    a memory having programming data storage locations accessed by the electrical stimulation therapy delivery circuit;
    an RF antenna; and
    a telemetry circuit coupled to the RF antenna and having a programming data output accessed by the memory; said telemetry circuit including an out-of-band rejection filter comprising a microelectromechanical filter.

2. The implantable medical device of claim 1 wherein the electrical stimulation therapy delivery circuit comprises cardiac pacemaker circuitry including a sense amplifier circuit, a stimulating pulse output circuit, a cardiac lead interface circuit coupled to the stimulating pulse output circuit, and a pacing timing and control circuit coupled to the sense amplifier and the stimulating pulse output circuit.

3. The implantable medical device of claim 1 wherein the out-of-band rejection filter is a bandpass filter.

4. The implantable medical device of claim 1 wherein the telemetry circuit further includes an amplifier coupled to the microelectromechanical filter and a demodulator coupled to the amplifier; and wherein the microelectromechanical filter, the amplifier and the demodulator are fabricated on a common integrated circuit die.

5. The implanted medical device of claim 1 wherein the telemetry circuit is a multichannel receiver comprising:
    an amplifier coupled to the RF antenna;
    a plurality of signal receiving circuits including a bandpass filter and a detector, each filter comprising a microelectromechanical narrowband, bandpass filter having a unique center frequency and constituting a particular receiver channel;
    a multiplexing circuit having a separate signal input coupled to each of the signal receiving circuits and a signal output providing access to a selected one of the signal inputs;
    an analog-to-digital converter coupled to the output of the multiplexing circuit and accepting a signal originating from the signal receiving circuit that is coupled to the selected multiplexing circuit input, the analog-to-digital converter having a multi-bit digital signal output providing a digitized sample of the accepted signal; and
    a processor operating in accordance with a set of program instructions to control the multiplexing circuit in providing sequential access of the analog-to-digital converter to each of the multiplexing circuit signal inputs, the processor further operating in accordance with the set of program instructions to evaluate the noise level of each channel and to make a selection of one of the channels for further communication with the external programming unit.

6. The implanted medical device of claim 1 wherein the telemetry circuit is a multichannel receiver comprising:
    an RF antenna;
    a plurality of microelectromechanical bandpass filters coupled to the RF antenna, each filter having a unique center frequency and defining an individual receiver channel;
    a multiplexing circuit coupled to the bandpass filters and having a signal output; and
    a programming data demodulator coupled to the signal output of the multiplexing circuit.

7. The implanted medical device of claim 6, wherein the multiplexing circuit has a control input connectable to a storage location within the memory to receive programming data defining selection of one of the bandpass filters for connection to the multiplexing circuit signal output.

8. An external programming unit for an implantable medical device operating in accordance with programming data received over a downlink communications channel established by a modulated RF transmission sent from the external programming unit and providing device information to the programming unit over an uplink communications channel established by a modulated RF transmission sent from the device, comprising:
    a housing carrying a display screen;
    a programming head including an RF antenna;
    a telemetry circuit disposed within the housing and coupled to the RF antenna, the telemetry circuit including an out-of-band rejection filter comprising a microelectromechanical filter.

9. The programming unit of claim 8 wherein the telemetry circuit is a multichannel receiver comprising:
    an amplifier coupled to the RF antenna;
    a plurality of microelectromechanical narrowband, bandpass filters of differing center frequency coupled to the amplifier and defining individual receiver channels;
    a multiplexing circuit having a separate signal input coupled to each of the bandpass filters and a signal output providing access to a selected one of the signal inputs;
    an analog-to-digital converter coupled to the output of the multiplexing circuit and accepting a signal originating from the bandpass filter that is coupled to the selected multiplexing circuit input, the analog-to-digital converter having a multi-bit digital signal output providing a digitized sample of the bandpass filter signal; and
    a processor operating in accordance with a set of program instructions to control the multiplexing circuit in providing access of the analog-to-digital converter to a signal from each of the bandpass filters and to obtain a digitized sample of the signal from each of the bandpass filters, the processor further operating in accordance with the set of program instructions to evaluate the signal-to-noise ratio of each channel and to make a selection of one of the channels for further communication with the implanted medical device.

10. A method of downlink telemetry communication from an external programming unit to an implantable medical device, comprising the steps of:

establishing a telemetry link between the external programming unit and the implantable medical device;

transmitting programming data from the external programming unit to the implantable medical device using a modulated RF transmission;

filtering the modulated RF transmission in the implantable medical device using an out-of-band rejection filter comprising a microelectromechanical filter; and demodulating the filtered RF transmission to obtain the transmitted programming data.

11. The method of claim 10 wherein the implantable medical device is a cardiac pacemaker.

12. The method of claim 10 wherein the filtering step comprises bandpass filtering.

13. A method of downlink telemetry communication from an external programming unit to an implantable medical device, comprising the steps of:

providing a plurality of out-of-band rejection filters in the implantable medical device, each filter comprising a microelectromechanical filter and each filter being tuned to a one of a plurality of different RF transmission carrier frequency channels;

determining a level of noise on each RF transmission carrier frequency channel;

selecting one of the filters as the preferred data transmission channel for further downlink telemetry communications based upon a determination of the noise level existing on each RF transmission carrier frequency channel;

establishing a telemetry link between the external programming unit and the implantable medical device on the selected RF transmission carrier frequency channel;

transmitting programming data from the external programming unit to the implantable medical device using a modulated RF transmission on the selected RF transmission carrier frequency channels;

applying the modulated RF transmission to the plurality of out-of-band rejection filters in the implantable medical device;

multiplexing signals passed by the out-of-band rejection filters to permit selection of one filter as the preferred data transmission channel; and demodulating the signals passed by the selected filter to recover the programming data.

14. The method of claim 13 wherein the implantable medical device is a cardiac pacemaker.

15. A method of identifying a preferred data transmission channel from among a plurality of different RF transmission frequency channels for downlink telemetry communication from an external programming unit to an implantable medical device, comprising the steps of:

providing a plurality of out-of-band rejection filters in the external programming unit, each filter comprising a microelectromechanical filter and each filter being tuned to a one of a plurality of different RF transmission carrier frequency channels to pass a signal within the passband of the filter;

multiplexing the signals passed by the out-of-band rejection filters;

sequentially accessing each of the multiplexed filter signals;

obtaining a digitized sample of each multiplexed filter signal when accessed;

storing the digitized signal samples;

processing the digitized signal samples to determine the noise level on each channel; and selecting one of the RF transmission frequency channels as a preferred data transmission channel for downlink telemetry communications sent to the implantable medical device.

16. The method of claim 15 wherein the implantable medical device is a cardiac pacemaker.

17. The method of claim 15 wherein the step of processing the stored samples to determine the noise level on each channel comprises making a determination of the signal-to-noise ratio of each channel.

18. A method of identifying a preferred data transmission channel from among a plurality of different RF transmission frequency channels for downlink telemetry communication from an external programming unit to an implantable medical device, comprising the steps of:

applying ambient signals obtained from an antenna to a broadband amplifier;

applying the amplified broadband ambient signals to a plurality of bandpass filters in the programming unit wherein each filter comprises a microelectromechanical filter tuned to pass signals at one of a plurality of different RF transmission frequency channels;

multiplexing signals passed by the filters to permit selection of a signal being passed by a particular one of the filters;

selecting each filter in the programming unit in sequence;

obtaining a digitized sample of the signal passed by each filter when selected;

storing the digitized signal samples; and processing the digitized signal samples obtained for each channel to determine the noise level on each channel; and selecting one of the RF transmission frequency channels for downlink telemetry communications sent to the implantable medical device.

* * * * *